United States Patent [19]

Sugiyama et al.

[11] Patent Number: 4,884,221

[45] Date of Patent: Nov. 28, 1989

[54] COLOR MEASURING APPARATUS

[75] Inventors: Masami Sugiyama, Toyonaka; Nobuyuki Kita, Osaka; Yoshihiro Tasaka, Nishinomiya, all of Japan

[73] Assignee: Minolta Camera Kabushiki Kaisha, Osaka, Japan

[21] Appl. No.: 38,366

[22] Filed: Apr. 14, 1987

[30] Foreign Application Priority Data

Apr. 14, 1986 [JP] Japan ................... 61-87535
Apr. 14, 1986 [JP] Japan ................... 61-87537

[51] Int. Cl.$^4$ .......................... G06F 15/20; G01J 3/50
[52] U.S. Cl. ................... 364/526; 364/571.01; 364/571.05; 356/407; 356/408
[58] Field of Search ............ 364/526, 571, 571.01, 364/571.05; 356/405, 408, 410, 402, 407; 250/226; 358/75; 8/400

[56] References Cited

U.S. PATENT DOCUMENTS

| | | | |
|---|---|---|---|
| 3,531,208 | 9/1970 | Ward .................... | 364/526 |
| 3,851,156 | 11/1974 | Green ................... | 304/526 |
| 4,029,419 | 6/1977 | Schomann et al. ....... | 364/526 |
| 4,300,689 | 11/1981 | Franklin et al. ........ | 356/407 |
| 4,367,041 | 1/1983 | Webb et al. ........... | 356/407 |
| 4,402,611 | 9/1983 | Yuasa ................... | 364/526 |
| 4,414,635 | 11/1983 | Gast et al. ............ | 356/405 |
| 4,597,670 | 7/1986 | Ohashi et al. .......... | 8/400 |
| 4,613,947 | 9/1986 | Suzuka et al. ......... | 364/526 |
| 4,648,051 | 3/1987 | Wandell et al. ........ | 364/526 |
| 4,653,014 | 3/1987 | Mikami et al. ........ | 356/406 |
| 4,688,178 | 8/1987 | Connelly et al. ...... | 364/526 |

FOREIGN PATENT DOCUMENTS

| | | |
|---|---|---|
| 56-77727 | 6/1981 | Japan . |
| 60-154124 | 8/1985 | Japan . |
| 60-178322 | 9/1985 | Japan . |
| 60-183530 | 9/1985 | Japan . |
| 60-186720 | 9/1985 | Japan . |
| 60-186721 | 9/1985 | Japan . |
| 60-186722 | 9/1985 | Japan . |

OTHER PUBLICATIONS

Catalog of Omron Tateisi Electronis Co. of Japan entitled "3Z4A Type Color Sensor", (1986).
Pamphlet of Macbeth of Japan entitled, "Macbeth MS-200 Spectrophotometer" and dated May of 1978.
Pamphlet of Macbeth of Japan entitled "Macbeth Color-Eye MS-4045 Online Color Control System" and dated May of 1985.
Pamphlet entitled "The Kent Jones and Martin Flour Colour Grader Series 3" (author and date of pub. unknown) (1986).

Primary Examiner—Parshotam S. Lall
Assistant Examiner—Ellis B. Ramirez
Attorney, Agent, or Firm—Price, Gess & Ubell

[57] ABSTRACT

A color measuring apparatus including a photoelectric conversion device for outputting basic color signals corresponding to quantities of light of basic color components of a sample, respectively, a calculating device for calculating a color value of the sample in a predetermined colorimetric system, a target setting device for setting a target color value of the sample in the predetermined colorimetric system, a region setting device for setting a predetermined region containing the target color value, a region decision device for deciding whether or not the color value falls within the predetermined region, an approximation decision device for deciding whether or not the color value has most approximated to the target color value and an output device for outputting a result of the decision of the approximation decision device.

20 Claims, 13 Drawing Sheets

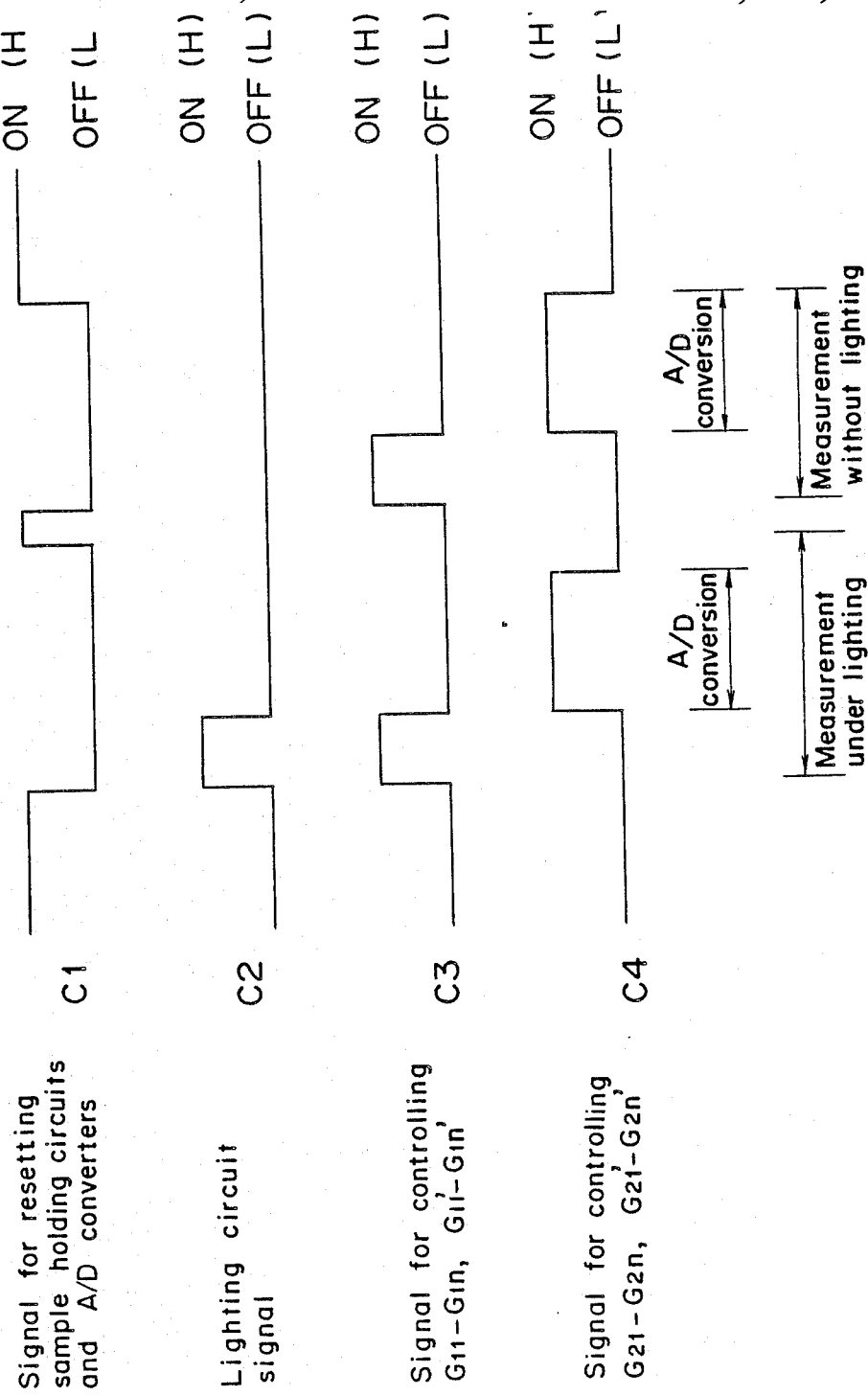

COLOR MEASURING APPARATUS

BACKGROUND OF THE INVENTION

1. Field of the Invention

The present invention relates to a color measuring apparatus for continuously measuring a color value of a sample, which is used for monitoring, for example, a change of a baked color with time due to baking or change of combination color through mixing of dyes.

2. Description of the Prior Art

Color measuring apparatuses are known which project ambient light onto surface of a sample and receive and analyze reflected light from the sample so as to discriminate color of the sample.

Meanwhile, in the case where a change of a baked color due to baking or a change of a combination color through mixing of dyes is continuously monitored by the known color measuring apparatuses such that the baking or the mixing of the dyes is stopped at the time when the measured color value of the sample has most approximated to a target color value, it can be considered that by calculating a distance between the measured color value and the target color value in two or three dimensions, a point of inflection at which the distance is shifted from a decreasing phase to an increasing phase, is detected so as to be regarded as representing a color value most approximate to the target color value. However, the measured color value does not necessarily approach to the target color value monotonously. Thus, if it is decided that an initial point of inflection appearing after the start of measurement represents the color value most approximate to the target color value, such a phenomenon as insufficient baking, etc. may take place. Hence, it is desirable to seek a point of inflection which can be regarded as really representing a color value most approximate to the target color value. Nonetheless, if such point of inflection is sought by neglecting so many points of inflection, such a state may also be created that the measured color value steadily departs from the target color value, thereby resulting in excessive baking, etc. In this case, it is understood that the baking, etc. should have been stopped at the previous point of inflection. Thus, in the case where the measured color value does not necessarily coincide with the target color value completely and the color value of the sample cannot be reinstated to the color value most approximate to the target color value after passing through the color value most approximate to the target color value, it is necessary to accurately detect the point of inflection which can be regarded as representing the color value most approximate to the target color value. However, the known color measuring apparatuses could not meet such requirements.

Furthermore, when a change of color of a sample is automatically measured repeatedly as in the case where change of baked color due to baking or change of combination color through mixing of dyes is monitored, a measuring time interval should be shortened, for the purpose of frequently collecting measured data, in a region in which the color of the sample is approximate to the target color value. However, in the known color measuring apparatuses, it is not so arranged that a time interval of automatic measurement is changed according to a color value of the sample. Thus, the known color measuring apparatuses have such a drawback that even in a region in which the color of the sample deviates far away from the target color value, automatic measurement is performed at a short time interval with the result that measured data is outputted frequently.

SUMMARY OF THE INVENTION

Accordingly, an essential object of the present invention is to provide a color measuring apparatus which can be operated with much ease through improvement of an automatic measurement of color of a sample.

Another object of the present invention is to provide a color measuring apparatus in which it can be simply decided that a color of the sample is the most approximated to a target color value.

Still another object of the present invention is to provide a color measuring apparatus in which amount of measured data on the color of the sample is decreased such that only the necessary measured data can be obtained.

BRIEF DESCRIPTION OF THE DRAWINGS

These objects and features of the present invention will become apparent from the following description taken in conjunction with the preferred embodiments thereof with reference to the accompanying drawings, in which:

FIG. 2 is a timing chart explanatory of light measuring operation of the color measuring apparatus of FIG. 1;

Before the description of the present invention proceeds, it is to be noted that like parts are designated by like reference numerals throughout several views of the accompanying drawings.

DETAILED DESCRIPTION OF THE PREFERRED EMBODIMENTS

Figure 1:
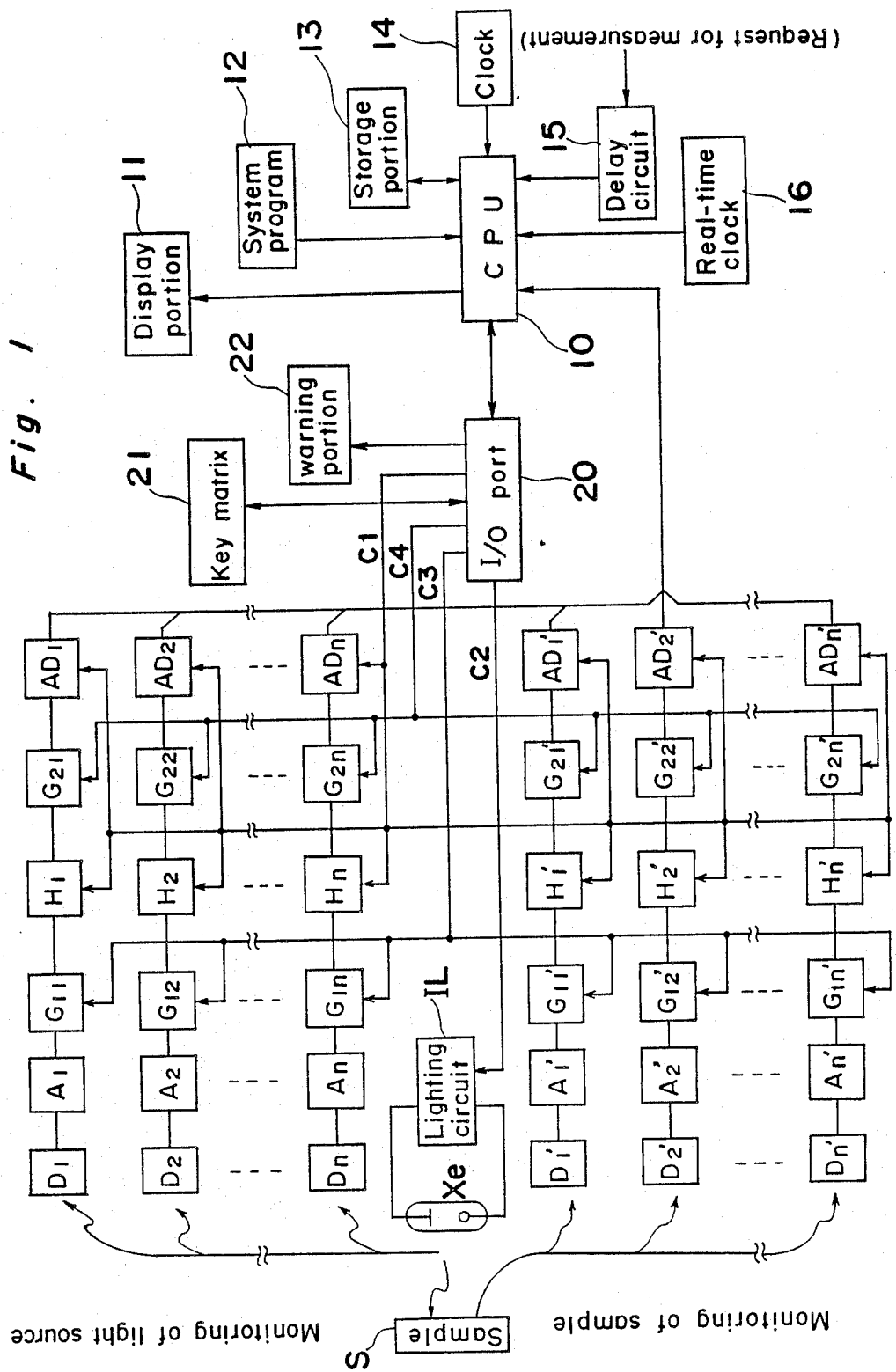
FIG. 1 is an electrical block diagram showing a whole arrangement of a color measuring apparatus according to a first embodiment of the present invention.

FIG. 1 is an electrical block diagram showing a photoelectric conversion portion and a control circuit of a color measuring apparatus according to a first embodiment of the present invention. The photoelectric conversion portion includes a lighting circuit IL for controlling the turning on and turning off of a pulse xenon tube Xe. Light from the pulse xenon tube Xe is projected onto a sample S. A part of light from the pulse xenon tube Xe is introduced to one side for monitoring a light source and is separated into basic color components by detection elements $D_1$ to $D_n$ (n=natural number) for detecting the basic color components so as to be subjected to photoelectric conversion into electric signals corresponding to the basic color components, respectively. Meanwhile, the other part of light from the sample S is introduced to another side for monitoring the sample S and is separated into basic color components by detection elements $D_1'$ to $D_n'$ for detecting the basic color components so as to be subjected to photoelectric conversion into electric signals corresponding to the basic color components, respectively.

The detection elements $D_1$ to $D_n$ and $D_1'$ to $D_n'$ are each constituted by a photodetector such as a photodiode or a photoelectric tube and a color filter for separating light into each of the basic color components, which is provided on a front face of the photodetector. The detection elements $D_1$ and $D_1'$, $D_2$ and $D_2'$,—, $D_n$ and $D_n'$ are, respectively, arranged to detect the same basic color components. In this embodiment, natural number n is set at 3 such that tristimulus values X, Y and Z are detected in a XYZ colorimetric system. Detection outputs of the detection elements $D_1$ to $D_n$ and $D_1'$ to $D_n'$ are, respectively, amplified to predetermined levels by amplification circuits $A_1$ to $A_n$ and $A_1'$ to $A_n'$ so as to be applied to sample holding circuits $H_1$ to $H_n$ and $H_1'$ to $H_n'$ through gate circuits $G_{11}$ to $G_{1n}$ and $G_{11}'$ to $G_{1n}'$. The signals sampled and held by the sample holding circuits $H_1$ to $H_n$ and $H_1'$ to $H_n'$ are, respectively, applied to A/D converters $AD_1$ to $AD_n$ and $AD_1'$ to $AD_n'$ via gate circuits $G_{21}$ to $G_{2n}$ and $G_{21}'$ to $G_{2n}'$. The light measuring values of the basic color components, which are converted into digital signals by the A/D converters $AD_1$ to $AD_n$ and $AD_1'$ to $AD_n'$, are inputted to a central processing unit (CPU) 10.

The CPU 10 is connected to a display portion 11, a system program memory 12, a storage portion 13 for storing information on color, etc., a clock circuit 14, a delay circuit 15, a real-time clock circuit 16 and an I/O port 20. The display portion 11 is provided for outputting measured data or displaying a target color value and is constituted by an LCD display, a printer or the like. The system program memory 12 stores a program to be executed by the CPU 10. The storage portion 13 is provided for storing the measured data of the basic color components, the target color value or a setting region and is constituted by a work area in a random access memory (RAM). The clock circuit 14 generates a system clock for actuating the CPU 10. In response to a request for measurement, the delay circuit 15 interrupts the CPU 10 upon lapse of a predetermined delay time so as to a start measuring operation. The delay time can be set to zero. The real-time clock circuit 16 is constituted by a clocking integrated circuit (IC), etc. so as to give to the CPU 10 data on measuring time, etc. The I/O port 20 is a circuit for performing input and output of data between the CPU 10 and its peripheral circuits. A key matrix 21 is connected to the I/O port 20 such that the target color value, data for setting a region containing the target color value, etc. can be inputted by operation of ten-key device of a keyboard. Furthermore, a warning portion 22 is connected to the I/O port 20 so as to issue a warning when an abnormal measuring operation is being performed. The I/O port 20 outputs a resetting signal C1 for resetting the sample holding circuits $H_1$ to $H_n$ and $H_1'$ to $H_n'$ and the A/D converters $AD_1$ to $AD_n$ and $AD_1'$ to $AD_n'$, a lighting circuit signal C2 for energizing or de-energizing the lighting circuit IL, a control signal C3 for controlling in enabling and disabling the gate circuits $G_{11}$ to $G_{1n}$ and $G_{11}'$ to $G_{1n}'$ and a control signal C4 for controlling in enabling and disabling the gate circuits $G_{21}$ to $G_{2n}$ and $G_{21}'$ to $G_{2n}'$.

Figure 3A:
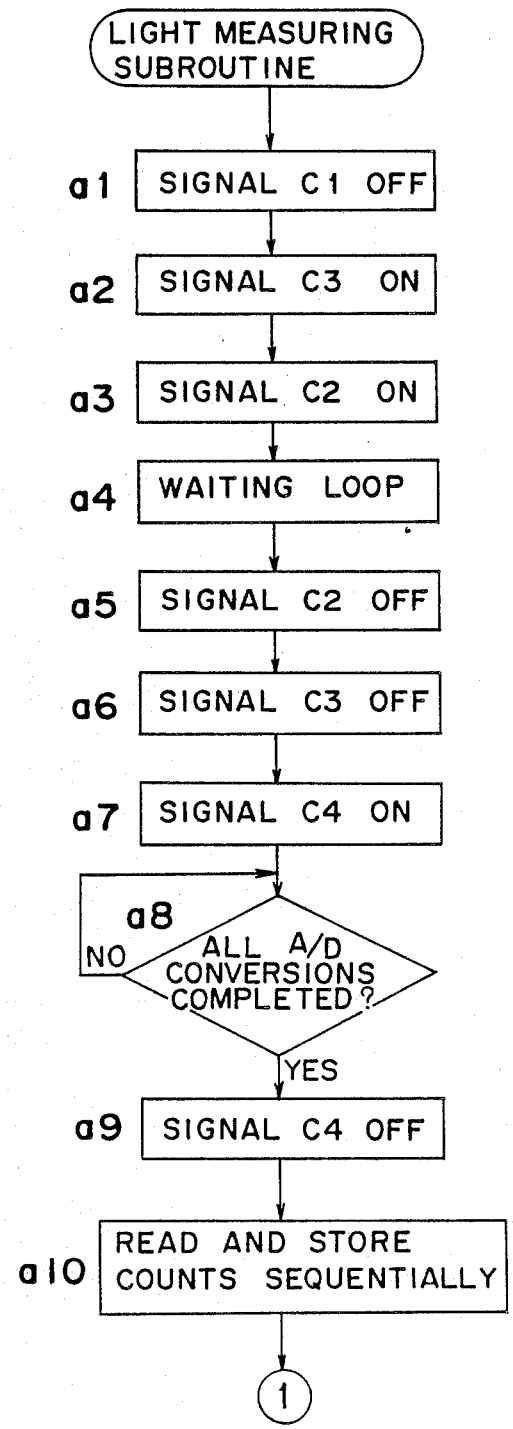
FIGS. 3A and 3B are flow charts showing a light measuring subroutine used in the color measuring apparatus of FIG. 1.
Figure 3B:
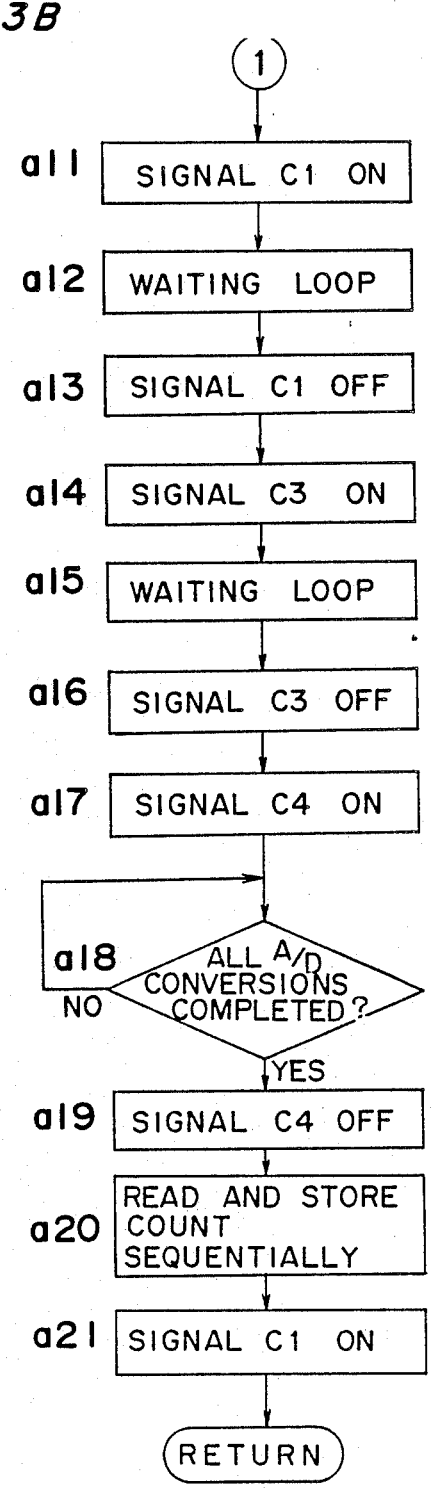

An operation of CPU 10 for reading data of the basic color components through measurement of the sample S is described with reference to a timing chart of FIG. 2 and flow charts of FIG. 3A and 3B. Initially, when a request for measurement is made, the CPU 10 sets the resetting signal C1 to the low state (OFF) at step a1 and then, sets the control signal C3 to the high state (ON) at step a2 so as to enable the gate circuits $G_{11}$ to $G_{1n}$ and $G_{11}'$ to $G_{1n}'$ such that information from the detection elements $D_1$ to $D_n$ at the side for monitoring the light source and from the detection elements $D_1'$ to $D_n'$ at the side for monitoring the sample S can be transmitted to the sample holding circuits $H_1$ to $H_n$ and $H_1'$ to $H_n'$. Subsequently, at step a3, the lighting circuit signal C2 is set to the high state (ON) so as to turn on the pulse xenon tube Xe. Upon lapse of a predetermined waiting time at step a4, the lighting circuit signal C2 is set to the low state (OFF) at step a5 so as to turn off the pulse xenon tube Xe and the control signal C3 is set to the low state (OFF) at step a6 so as to disable the gate circuits $G_{11}$ to $G_{1n}$ and $G_{11}'$ to $G_{1n}'$. Then, at step a7, the control signal C4 is set to the high state (ON) so as to enable the gate circuits $G_{21}$ to $G_{2n}$ and $G_{21}'$ to $G_{2n}'$ such that information sampled and held by the sample holding circuits $H_1$ to $H_n$ to $H_1'$ to $H_n'$ is transmitted to the A/D converters $AD_1$ to $AD_n$ and $AD_1'$ to $AD_n'$. The A/D converters $AD_1$ to $AD_n$ and $AD_1'$ to $AD_n'$ convert, for example, the above described sampled and held information into information of pulse widths corresponding to the sampled and held imformation, and count the number of clocks during periods of the pulse widths, by using digital counters, so as to convert the sampled and held information into corresponding digital signals. If it is found at step a8 that all the A/D conversions have been completed, the control signal C4 is set to the low state (OFF) at step a9 and then, at step a10, the CPU 10 sequentially reads counts of the counters and stores the counts in its storage area. The counts of the light measuring data at the side for monitoring the light source are sequentially stored in storage areas of array variables FR(1) to FR(n), respectively. Meanwhile, the counts of the light measuring data at the side for monitoring the sample S are stored in storage areas of array variables FS(1) to FS(n), respectively. The above described steps indicate light measurement under lighting.

Subsequently, light measurement without lighting is performed. Initially, the resetting signal C1 is set to the high state (ON) at step a11 and held in the high state (ON) for a predetermined time period at steps a12 and a13 such that the information stored in the sample holding circuits $H_1$ to $H_n$ and $H_1'$ to $H_n'$ is cancelled and the counters of the A/D converters $AD_1$ to $AD_n$ and $AD_1'$ to $AD_n'$ are reset. Then, the control signal C3 is set to the high state (ON) at step a14 and is held in the high state (ON) for a predetermined time period at steps a15 and a16 so as to enable the gate circuits $G_{11}$ to $G_{1n}$ and $G_{11}'$ to $G_{1n}'$ for the predetermined time period such that the information of the detection elements $D_1$ to $D_n$ and $D_1'$ to $D_n'$ is transmitted to the sample holding circuits $H_1$ to $H_n$ and $H_1'$ to $H_n'$, respectively. Subsequently, at step a17, the control signal C4 is set to the high state (ON) so as to enable the gate circuits $G_{21}$ to $G_{2n}$ and $G_{21}'$ to $G_{2n}'$ such that the information stored in the sample holding circuits $H_1$ to $H_n$ and $H_1'$ to $H_n'$ is transmitted to the A/D converters $AD_1$ to $AD_n$ and $AD_1'$ to $AD_n'$ to be counted as digital signals. If it is found at step a18 that all the A/D conversions of the A/D converters $AD_1$ to $AD_n$ and $AD_1'$ to $AD_n'$ have been completed, the control signal C4 is set to the low state (OFF) at step a19 so as to disable the gate circuits $G_{21}$ to $G_{2n}$ and $G_{21}'$ to $G_{2n}'$. Then, at step a20, the CPU 10 sequentially reads the above described counts and stores the counts in its storage areas. At this time, the data at the side for monitoring the light source are, respectively, stored in storage areas of array variables DR(1) to DR(n), while the data at the side for monitoring the sample S are, respectively, stored in storage areas of array variables DS(1) to DS(n). Finally, the resetting signal C1 is set to the high state (ON) at step a21 such that arithmetic operation of the respective data is started.

Then, the arithmetic operation of the data is described. Initially, difference between the measured data under lighting and the measuring data without lighting is calculated such that data free from effects of the external light are obtained. Supposing that character i denotes a variable from 1 to n, the obtained results of the data at the side for monitoring the light source are, respectively, stored in array variables MR(i), while the obtained results of the data at the side for monitoring the sample S are, respectively, stored in array variables MS(i). Namely, $$MR(i) = FR(i) - DR(i)$$

$$MS(i) = FS(i) - DS(i)$$

Then, the data at the side for monitoring the sample S are divided by the data at the side for monitoring the light source such that effects of change of quantity of light emitted by the light source, etc. are cancelled from the data for monitoring the sample S. Results obtained by dividing the data at the side for monitoring the sample S by the data at the side for monitoring the light source are stored in array variables ANS(i), respectively. Namely, $$ANS(i) = MS(i)/MR(i)$$

The tristimulus values X, Y and Z are calculated by using the array variables ANS(i) and are converted into corresponding chromaticity coordinates on XYZ colorimetric system such that the color value is displayed or printed.

Figure 6:
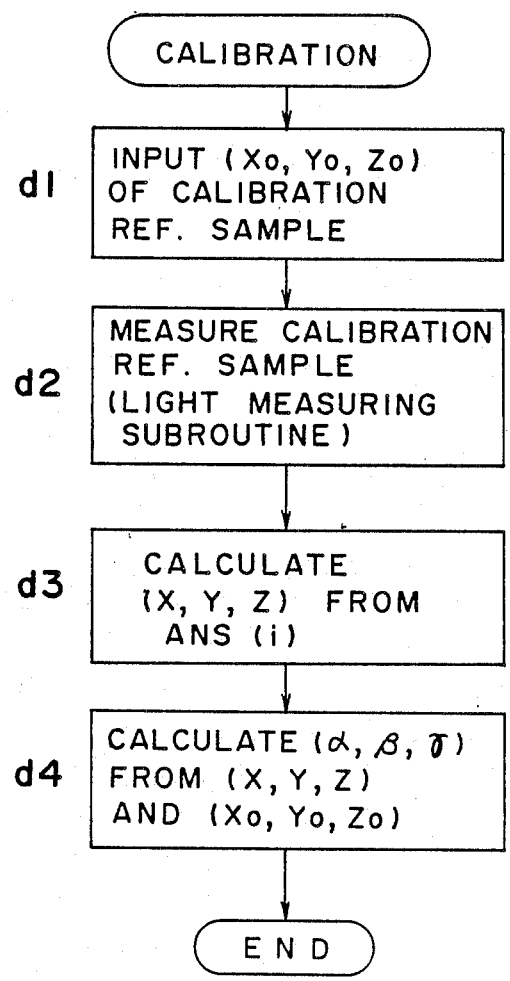
FIG. 6 is a flow chart showing a calibration routine used in the color measuring apparatus of FIG. 1.

In this color measuring apparatus, calibration is required to be performed before use of the color measuring apparatus. FIG. 6 shows a routine for performing the calibration. Initially, at step d1, tristimulus values $(X_o, Y_o, Z_o)$ of a calibration reference sample are inputted from the keyboard. Subsequently, the calibration reference sample is measured at step d2. Then, at step d3, the tristimulus values (X, Y, Z) are calculated by the above described steps. Thereafter, at step d4, calibration factors $(\alpha, \beta, \gamma)$ for the tristimulus values (X, Y, Z) are calculated by using the following equations.

$$\alpha = X_o/X, \beta = Y_o/Y, \gamma = Z_o/Z$$

Figure 5A:
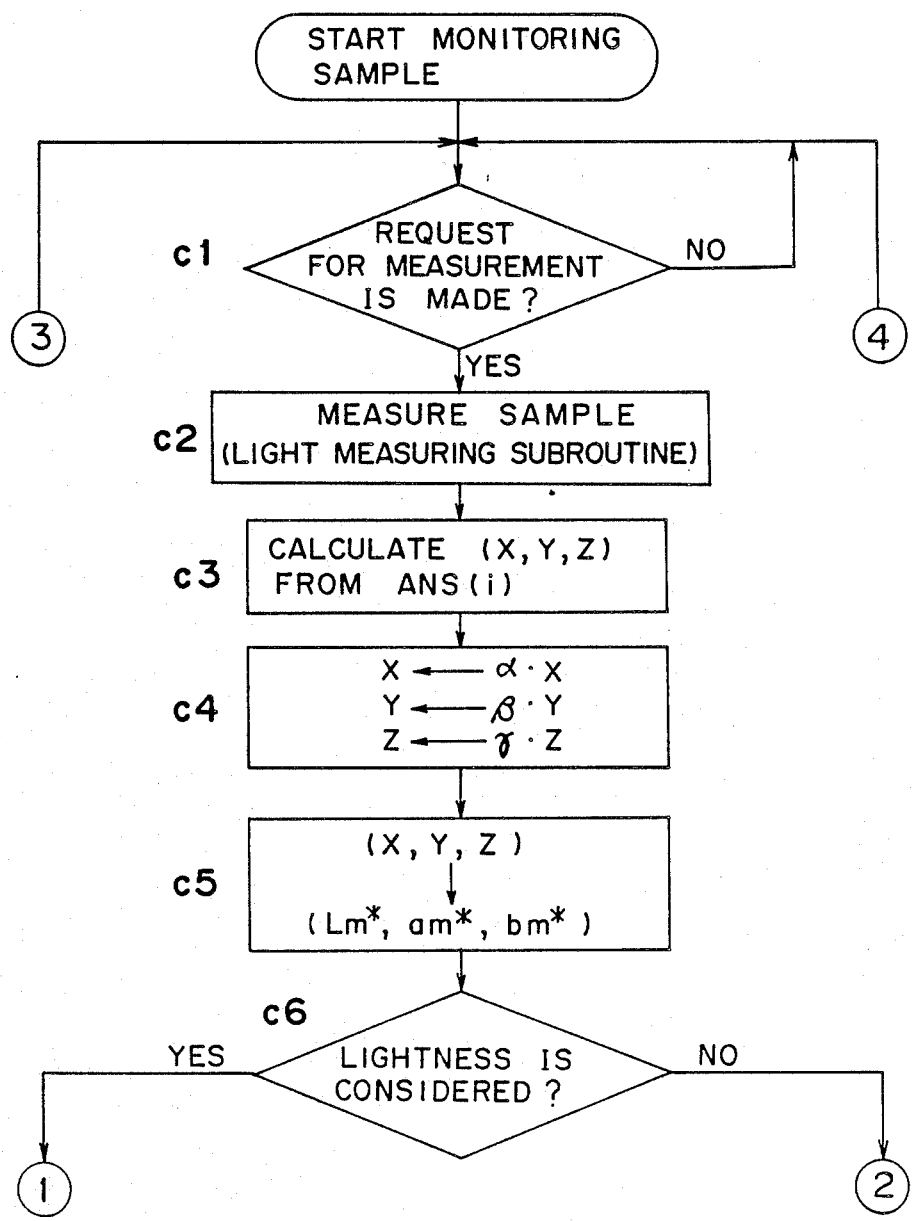
FIGS. 5A, 5B and 5C are flow charts showing a sample monitoring routine used in the color measuring apparatus of FIG. 1.
Figure 5B:
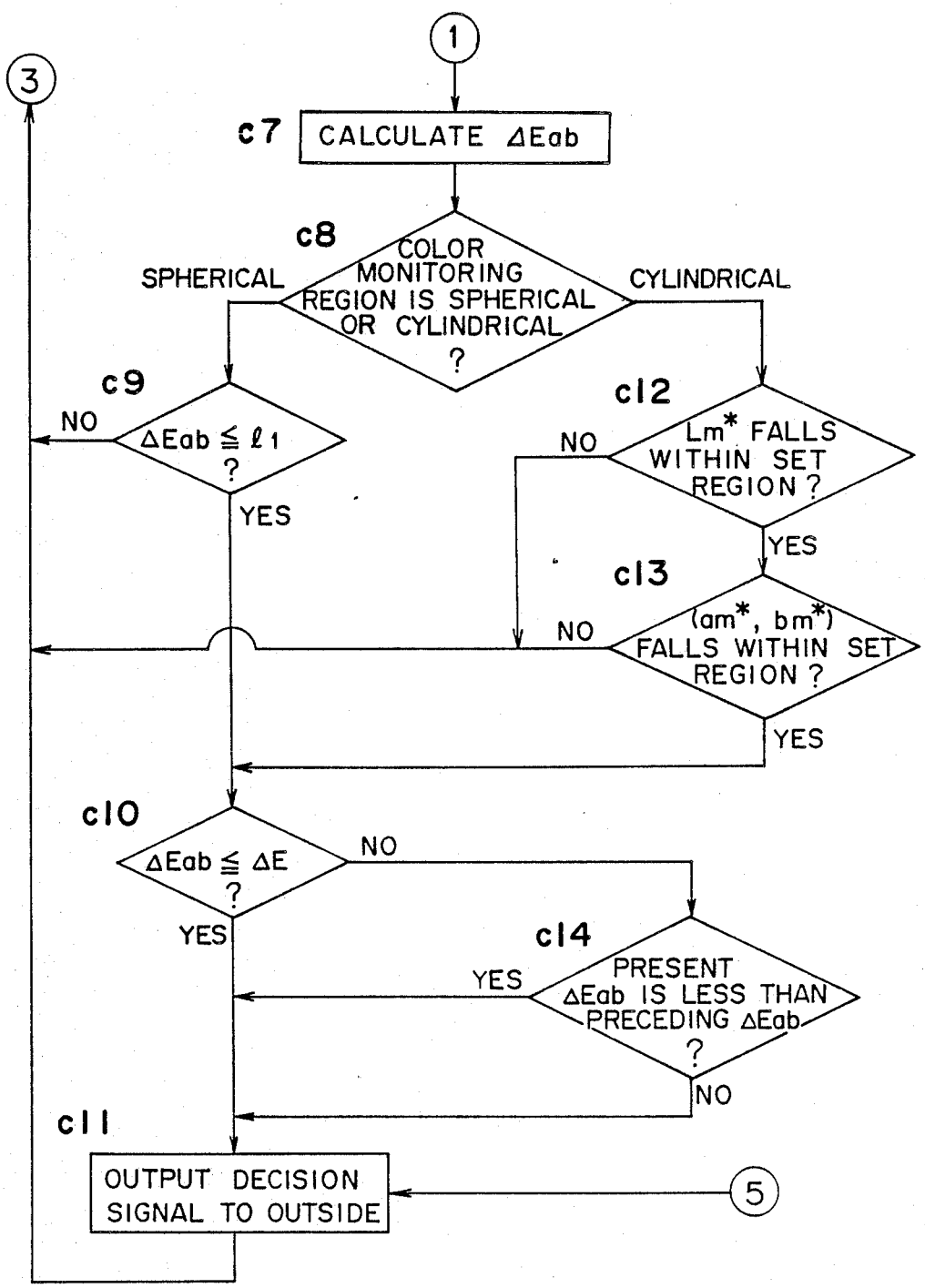
Figure 5C:
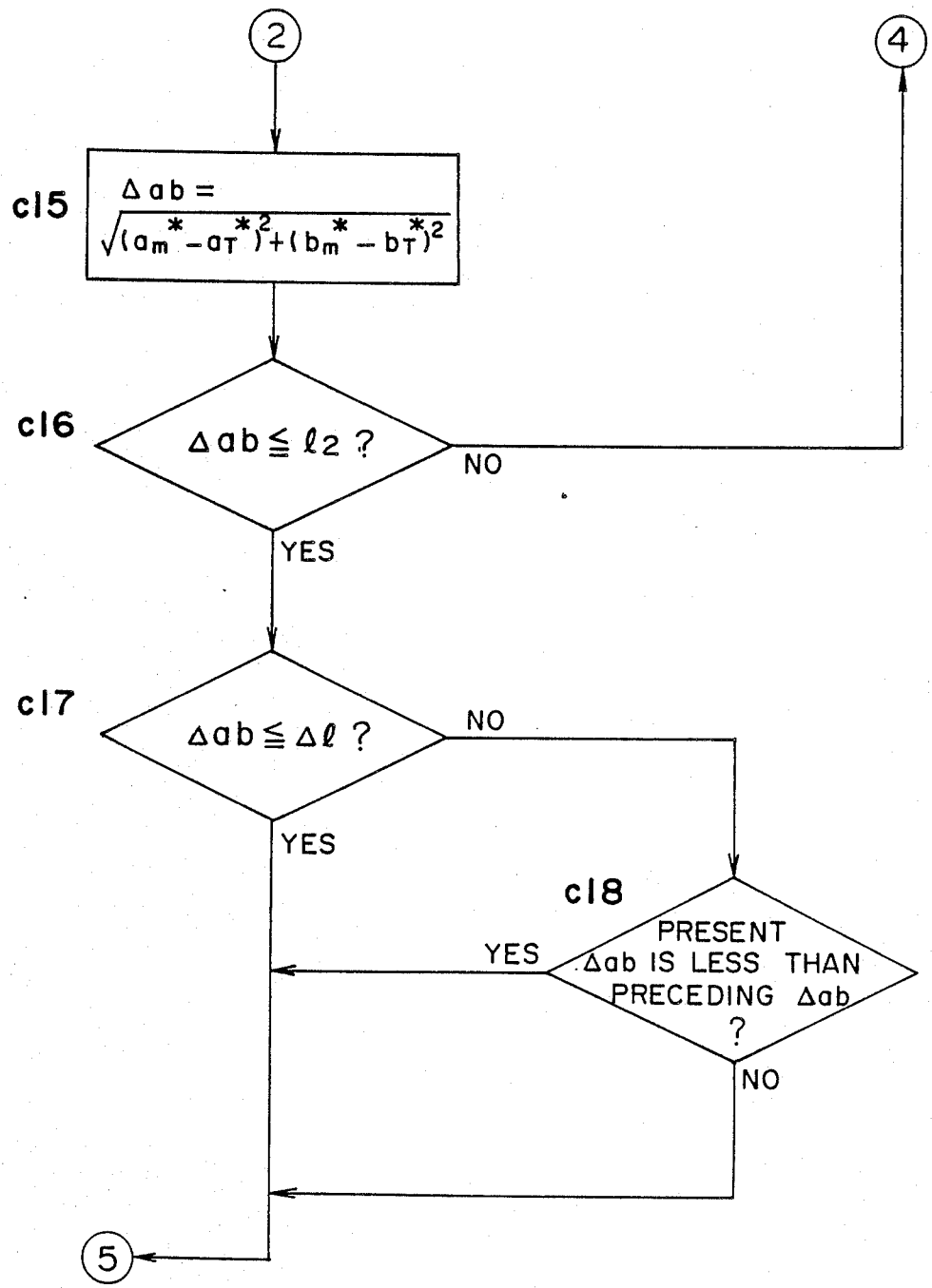

At the time of measurement of the sample after the calibration, a light measuring subroutine of FIGS. 5A to 5C is executed. Thus, as will be described in detail later, the tristimulus values (X, Y, Z) are calculated by the above described steps. Furthermore, the tristimulus values are, respectively, multiplied by the calibration factors $(\alpha, \beta, \gamma)$ and the results of the multiplication are set as new tristimulus values such that the new tristimulus values are converted into chromaticity coordinates on predetermined XYZ colorimetric system.

Figure 4A:
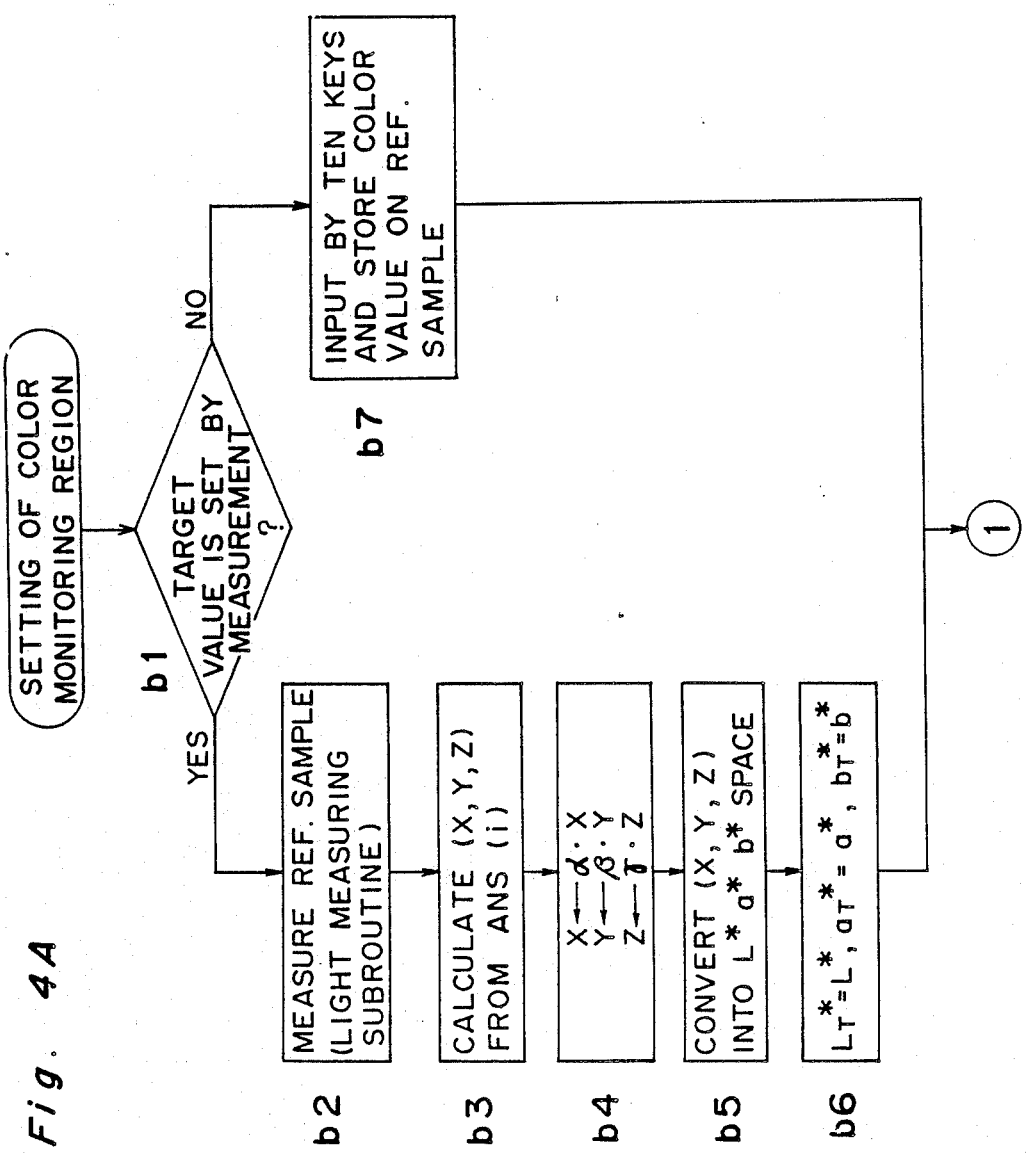
FIGS. 4A and 4B are flow charts showing a region setting routine used in the color measuring apparatus of FIG. 1.
Figure 4B:
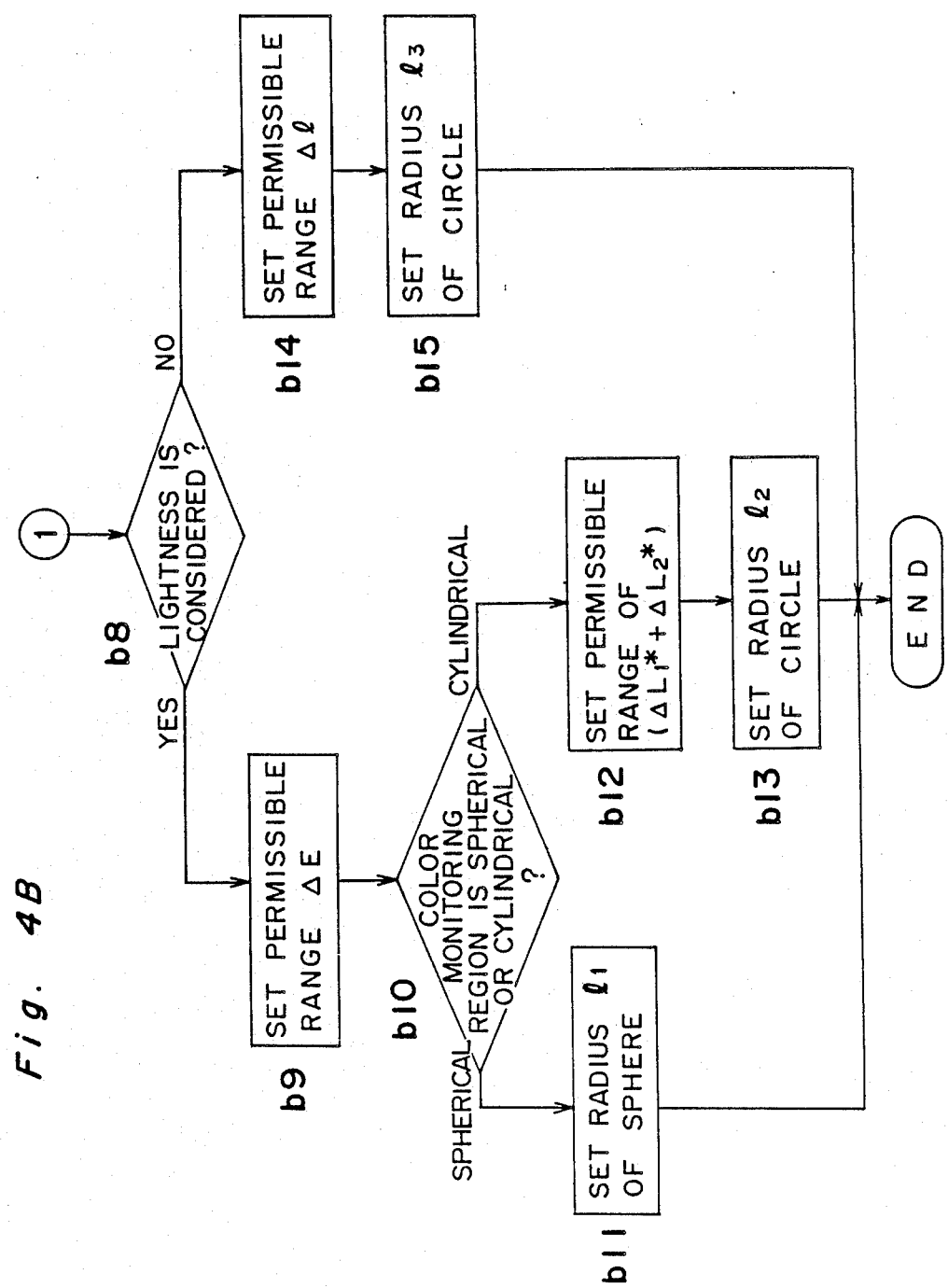

Then, a method of setting a region for monitoring whether or not the measured color value of the sample S has been most approximated to the target color value. FIGS. 4A and 4B are flow charts showing a routine for setting this region. In this routine, a predetermined region is set in an $L^*a^*b^*$ colorimetric system. However, it can also be so arranged that the region is set in other colorimetric systems than the $L^*a^*b^*$ colorimetric system. In the routine of FIGS. 4A and 4B, in order to set the region, a target value $(L_T^*, a_T^*, b_T^*)$ is set in chromaticity coordinates defined by the $L^*a^*b^*$ colorimetric system. Then, one portion falling within a predetermined distance of the target value is regarded as being in the region, while the other portion falling out of the predetermined distance of the target value is regarded as being out of the region. Setting of the target value is performed by either measurement or operation of a ten-key device. If it is found at step b1 that the target value is set by measurement, the above described light measuring subroutine is executed for a target reference sample such that the reference sample is measured at step b2. From the results ANS(i) obtained at step b2, the tristimulus values (X, Y, Z) are calculated at step b3. Then, at step b4, the tristimulus values (X, Y, Z) are multiplied by the calibration factors $(\alpha, \beta, \gamma)$ obtained in the calibration routine referred to earlier such that the results of the multiplication are set as new tristimulus values (X, Y, Z). Subsequently, at step b5, the new tristimulus values (X, Y, Z) are converted into the chromaticity coordinates defined by the $L^*a^*b^*$ colorimetric system. Then, at step b6, the results of the conversion are set as the target color value $(L_T^*, a_T^*, b_T^*)$. Meanwhile, if it is found at step b1 that the target value is set by operation of ten-key device, data of the color value of the target reference sample are inputted by operation of the ten-key device and the inputted data are stored as the color value $(L_T^*, a_T^*, b_T^*)$ of the target reference sample at step b7.

In the routine of FIGS. 4A and 4B, a boundary of the region is determined by the distance from the target color value. A method of setting the region is changed according to whether or not lightness $L^*$ is considered in the decision of the boundary of the region. Initially, if it is found at step b8 that the lightness $L^*$ is considered in the decision of the boundary of the region, a permissible range $\Delta E$ in which the color value of the sample to be measured can be construed as having most approximated the value of the target color value is set at step b9. Then, if it is found at step b10 that a sphere having the target color value at its center is employed as the monitoring region in the chromaticity coordinates, a radius l1 of the sphere is set at step b11. Meanwhile, if it is found at step b10 that a cylinder having the chromaticity point $(a_T^*, b_T^*)$ of the target color value at its axis is employed as the monitoring region in the chromaticity coordinates, permissible ranges $\Delta L_1^*$ and $\Delta L_2^*$ for the element $L_T^*$ of the target color value $(L_T^*, a_T^*, b_T^*)$ are set in positive and negative directions, respectively at step b12 such that a height of the cylinder is determined as $(\Delta L_1^* + \Delta L_2^*)$. Furthermore, at step b13, a radius l2 of a circle having the chromaticity point $(a_T^*,$ $b_T^*$) of the target color value at its center is set at step b13 such that a radius of the cylinder is determined.

Then, if it is found at step b8 that the lightness $L^*$ is not considered in the decision of the boundary of the region, a permissible range $\Delta l$ in which the color value of the sample can be construed as having most approximated the value of the target color value is set in the chromaticity region at step b14. Then, at step b15, a radius l3 of a circle having the chromaticity point ($a_T^*$, $b_T^*$) of the target color value at its center is set such that the circle defines the boundary of the monitoring region.

In addition, in order to set the monitoring region, such a method can also be employed in which upper and lower limits of one of the elements $L^*$, $a^*$ and $b^*$ are set. Furthermore, such a method can also be employed therefor in which upper and lower limits of two or all of the elements $L^*$, $a^*$ and $b^*$ are set such that the respective AND or OR conditions or their combination is utilized.

After the above described settings have been performed, a routine of FIGS. 5A, 5B and 5C is executed so as to monitor color of the sample. Flow charts of FIGS. 5A, 5B and 5C are connected with each other by connectors ① to ⑤. Initially, in the flow chart of FIG. 5A, a decision is made at step c1 as to whether or not a request for measurement is made. In the case of "YES" at step c1, the light measuring subroutine referred to earlier with reference to FIGS. 3A and 3B is performed at step c2 so as to measure the sample. Then, at step c3, the tristimulus values (X, Y, Z) are calculated from the obtained results ANS(i). Subsequently, at step c4, the tristimulus values (X, Y, Z) are, respectively, multiplied by the calibration factors ($\alpha$, $\beta$, $\gamma$) such that the results of the multiplication are newly set as the tristimulus values (X, Y, Z). Then, at step c5, the obtained tristimulus values (X, Y, Z) are converted into chromaticity coordinates defined by the $L^*a^*b^*$ colorimetric system such that a measured color value ($Lm^*$, $am^*$, $bm^*$) is obtained. A decision as to whether or not the measured color value falls within the set region is made based on two cases, namely one case of FIG. 5B in which the lightness $L^*$ is considered and the other case of FIG. 5C in which the lightness $L^*$ is not considered.

Initially, if it is found at step c6 that the lightness $L^*$ is considered, a difference $\Delta Eab$ between the color value of the sample and the target color value is calculated at step c7 by using the following equation.

$$\Delta Eab = \sqrt{(Lm^* - L_T^*)^2 + (am^* - a_T^*)^2 + (bm^* - b_T^*)^2}$$

Then, if it is found at step c8 that the color monitoring region is spherical, a decision is made at step c9 as to whether or not the color difference value $\Delta Eab$ is equal to or less than the radius l1 of the sphere. In the case of "NO" at step c9, it is decided that the color value of the sample does not fall within the monitoring region, so that a decision as whether or not the color value of the sample has most approximated the value of the target color value is not made and thus, the result of the decision is not outputted. In the case of "YES" at step c9 a decision is made at step c10 as to whether or not the color difference value $\Delta Eab$ is equal to or less than the permissible range $\Delta E$. In the case of "YES" at step c10, it is decided that the measured color value has most approximated to the target color value and thus, this decision signal is outputted externally at step c11. The program flow returns from step c11 to step c1. Meanwhile, in the case of "NO" at step c10, a decision is made at step c14 as to whether or not the present color difference value $\Delta Eab$ is less than the preceding color difference value $\Delta Eab$. In the case of "YES" at step c14, it is decided that the measured color value of the sample is so changed as to approximate the target color value and thus, this decision signal is outputted externally at step c11. On the contrary, in the case of "NO" at step c14, it is decided that the measured color value of the sample is so changed as to deviate away from the target color value and thus, this decision signal is outputted externally at step c11. It is to be noted here that an initial decision signal to the effect that the measured color value of the sample is so changed as to deviate away from the target color value functions as a signal indicating that the measured color value of the sample is at its most approximated value to the target color value.

On the other hand, if it is found at step c8 that the color monitoring region is cylindrical, a decision is made at step c12 as to whether or not the lightness $L_m^*$ falls within the set region, i.e. between the lower limit ($L_T^* - \Delta L_2^*$) and the upper limit ($L_T^* + \Delta L_1^*$). In the case of "YES" at step c12, a decision is made at step c13 as to whether or not the chromaticity point ($am^*$, $bm^*$) falls within the set region, i.e. in the circle having the radius l2 and having the chromaticity point ($a_T^*$, $b_T^*$) of the target color value at its center by using the following equation.

$$\sqrt{(am^* - a_T^*)^2 + (bm^* - b_T^*)^2} \leq l2$$

In the case of "YES" at step c13, the program flow proceeds to step c10. Meanwhile, in the case of "NO" at step c13, the program flow returns to step c1. The above described steps are repeated as far as a request for measurement is made at step c1.

Meanwhile, if it is found at step c6 that the lightness $L^*$ is not considered in a decision as to whether or not the measured color value falls within the set region, a color difference value $\Delta ab$ between the measured color value of the sample and the target color value is calculated in the chromaticity region ($a^*$, $b^*$) at step c15 by using the following equation.

$$\Delta ab = \sqrt{(am^* - a_T^*)^2 + (bm^* - b_T^*)^2}$$

Then, a decision is made at step c16 as to whether or not the color difference value $\Delta ab$ is equal to or less than the radius l2 of the circle. In the case of "NO" at step c16, it is decided that the color value of the sample does not fall within the monitoring region, so that a decision is not made as to whether or not the color value of the sample has most approximated the target value and the result of this decision is not outputted. In the case of "YES" at step c16, a decision is made at step c17 as to whether or not the color difference value $\Delta ab$ is equal to or less than a permissible range $\Delta l$ in which the measured color value of the sample can be regarded as having reached its most approximated value to the target color value. In the case of "YES" at step c17, it is decided that the measured color value of the sample has reached its most approximated value to the target color value and thus, this decision signal is outputted externally at step c11. On the contrary, in the case of "NO" at step c17, a decision is made at step c18 as to whether or not the present color difference value $\Delta ab$ is less than the preceding color difference value $\Delta ab$. In the case of "YES" at step c18, it is decided that the measured color value of the sample is so changed as to approximate to the target color value and thus, this decision signal is outputted externally at step c11. On the other hand, in the case of "NO" at step c18, it is decided that the measured color value of the sample is so changed as to deviate away from the target color value and thus, this decision signal is outputted externally at step c11. Also in this case, an initial signal to the effect that the measured color value of the sample is so changed as to deviate away from the target color value functions as a signal indicating that the measured color value of the sample has reached its most approximated value to the target color value.

Meanwhile, it can be so modified that after the measured color value of the sample has fallen within the set region, a locus, points of inflection, rates of change, etc. of the measured color value of the sample are measured such that signals indicative of the measurements are outputted.

As is clear from the foregoing description, the region containing the target color value is set in the chromaticity coordinates such that a decision is made as to whether or not the measured color value of the sample has reached its most approximated color value to the target color value when it was found that the measured color value of the sample falls within the set region. Therefore, since the means for deciding whether or not the measured color value of the sample has been most approximated in value to the target color value is not actuated before the measured color value of the sample falls within the set region containing the target color value, the signal for detecting that the measured color value of the sample has most approximated the value to the target color value is not outputted. Meanwhile, since the means for deciding whether or not the measured color value of the sample has reached its most approximated color value to the target color value is actuated after the measured color value of the sample has fallen within the set region containing the target color value, the signal for detecting that the measured color value of the sample has been most approximated to the target color value is outputted when the distance between the measured color value and the target color value has changed from a decreasing phase to an increasing phase, so that the measured color value which has been most approximated to the target color value can be detected accurately.

Figure 7:
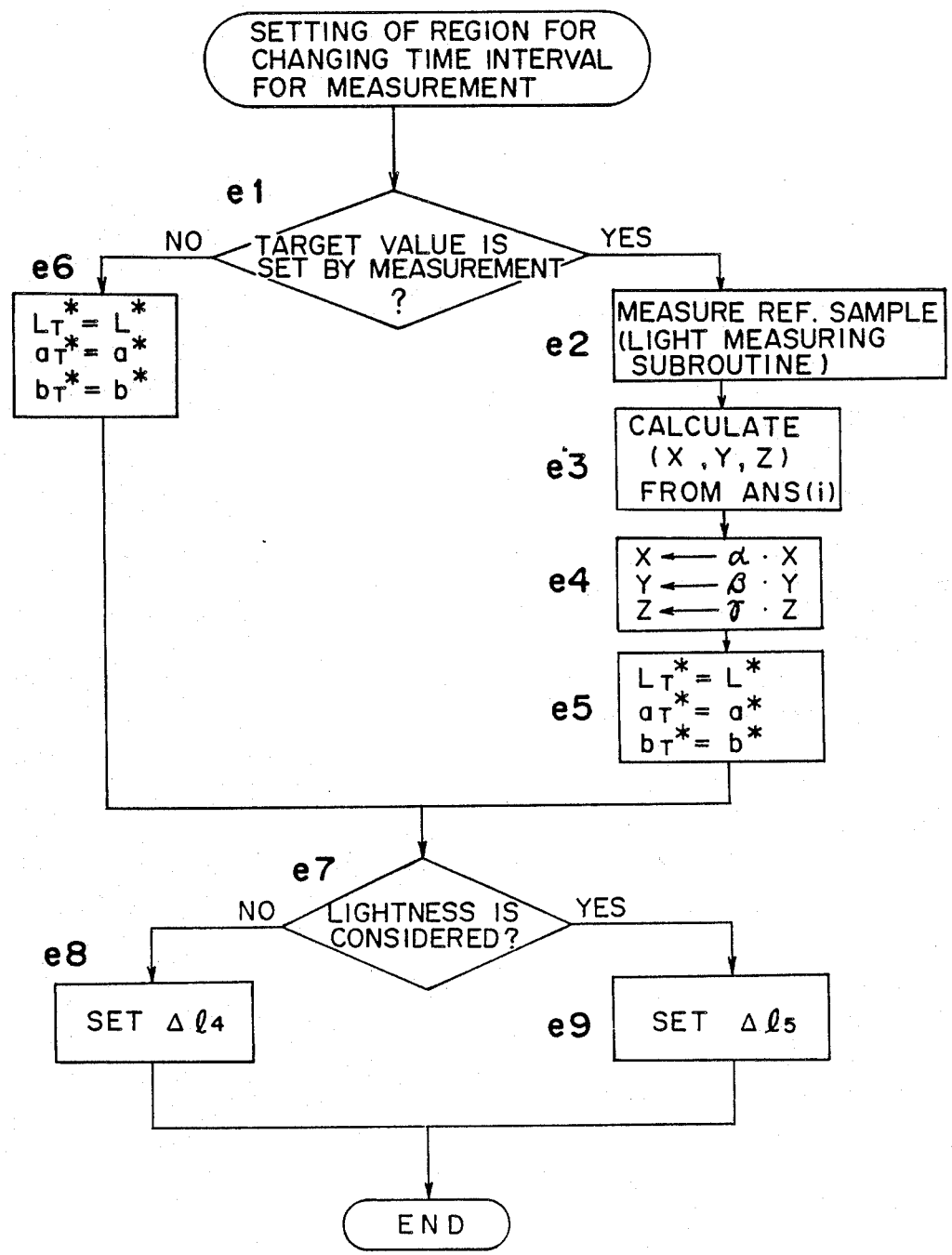
FIG. 7 is a flow chart showing a region setting routine used in a color measuring apparatus according to a second embodiment of the present invention.

Hereinbelow, a second embodiment of the present invention is described with reference to FIGS. 7 to 9. It should be noted that FIGS. 1, 2, 3 and 6 are likewise applied to the second embodiment. Initially, a method of setting a region for changing a time interval for measuring the sample S is described with reference to FIG. 7. FIG. 7 is a flow chart showing the routine for setting the region. In the routine of FIG. 7, the predetermined region is set in the $L^*a^*b^*$ colorimetric system but can also be set in other colorimetric systems than the $L^*a^*b^*$ colorimetric system. In the routine of FIG. 7, in order to set the region, a target value ($L_T^*$, $a_T^*$, $b_T^*$) is set in chromaticity coordinates defined by the $L^*a^*b^*$ colorimetric system. Thus, in the chromaticity coordinates, a portion falling within a predetermined distance of the target value is regarded as being in the region and another portion falling out of the predetermined distance of the target value is regarded as being out of the region. Setting of the target value is performed by measurement or operation of the ten-key device. If it is found at step e1 that the target value is set by measurement, the light measuring subroutine of FIG. 3 is executed on a target reference sample at step e2 so as to measure the reference sample. Then, at step e3, the tristimulus values (X, Y, Z) are calculated from the results ANS(i) obtained by the measurement of step e2. Subsequently, at step e4, the tristimulus values are, respectively, multiplied by the calibration factors ($\alpha$, $\beta$, $\gamma$) obtained in the calibration routine of FIG. 6 such that the results of the multiplication are newly set as the tristimulus values (X, Y, Z). Thereafter, at step e5, the new tristimulus values (X, Y, Z) are converted into chromaticity coordinates defined by the $L^*a^*b^*$ colorimetric system and the results of the conversion are stored as the target color value ($L_T^*$, $a_T^*$, $b_T^*$). Meanwhile, if it is found at step e1 that the target color value is set by operation of a ten-key device, data of the color value of the target reference sample are inputted by operation of the ten-key device and the inputted data are stored as the target color value ($L_T^*$, $a_T^*$, $b_T^*$) at step e6.

In the routine of FIG. 7, a boundary of the region is set according to a distance from the target color value. A method of setting the region is changed according to whether or not the lightness $L^*$ is considered in decision of the boundary of the region. If it is found at step e7 that the lightness $L^*$ is not considered in the decision of the boundary of the region, a circle having the chromaticity point ($a_T^*$, $b_T^*$) of the target value in the chromaticity region as its center and having a radius $\Delta l4$ is formed at step e8 so as to define the boundary of the region. On the other hand, if it is found at step e7 that the lightness $L^*$ is considered in the decision of the boundary of the region, a sphere having the target color value ($L_T^*$, $a_T^*$, $b_T^*$) as its center and having a radius $\Delta l5$ is formed at step e9 such that a spherical surface of the sphere defines the boundary of the region.

In addition, in order to set the region, such a method can also be employed in which upper and lower limits of one of the elements $L^*$, $a^*$ and $b^*$ are set. Furthermore, such a method can also be employed therefor in which upper and lower limits of two or all of the elements $L^*$, $a^*$ and $b^*$ are set such that the respective AND or OR conditions or their combination is utilized.

Figure 9:
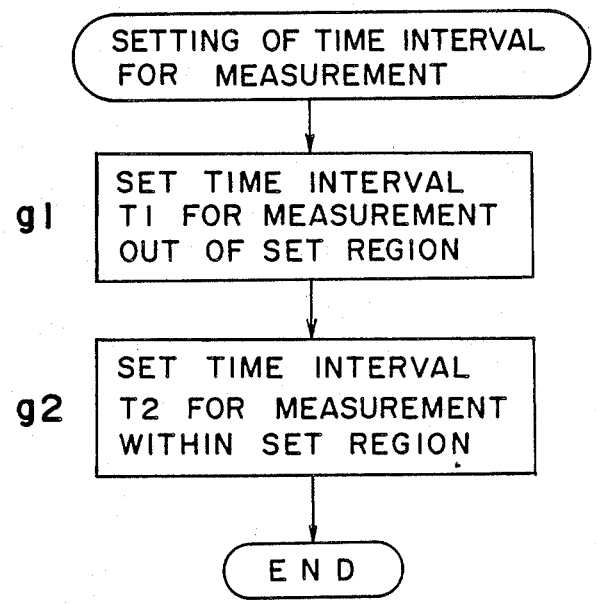
FIG. 9 is a flow chart showing a routine for setting a measuring time interval for the color measuring apparatus of FIG. 7.

After the boundary of the region has been set as described above, a routine for setting the time interval for measurement is executed as shown in FIG. 9. In the routine of FIG. 9, in the case of measurement out of the region defined by the above described boundary, a time interval T 1 for measurement is set at step g1. Meanwhile, in the case of measurement in the region, a time interval T2 for measurement, which is different from the time interval T 1, is set at step g2. The time intervals T 1 and T 2 can be set by operation of the ten-key device.

Figure 8:
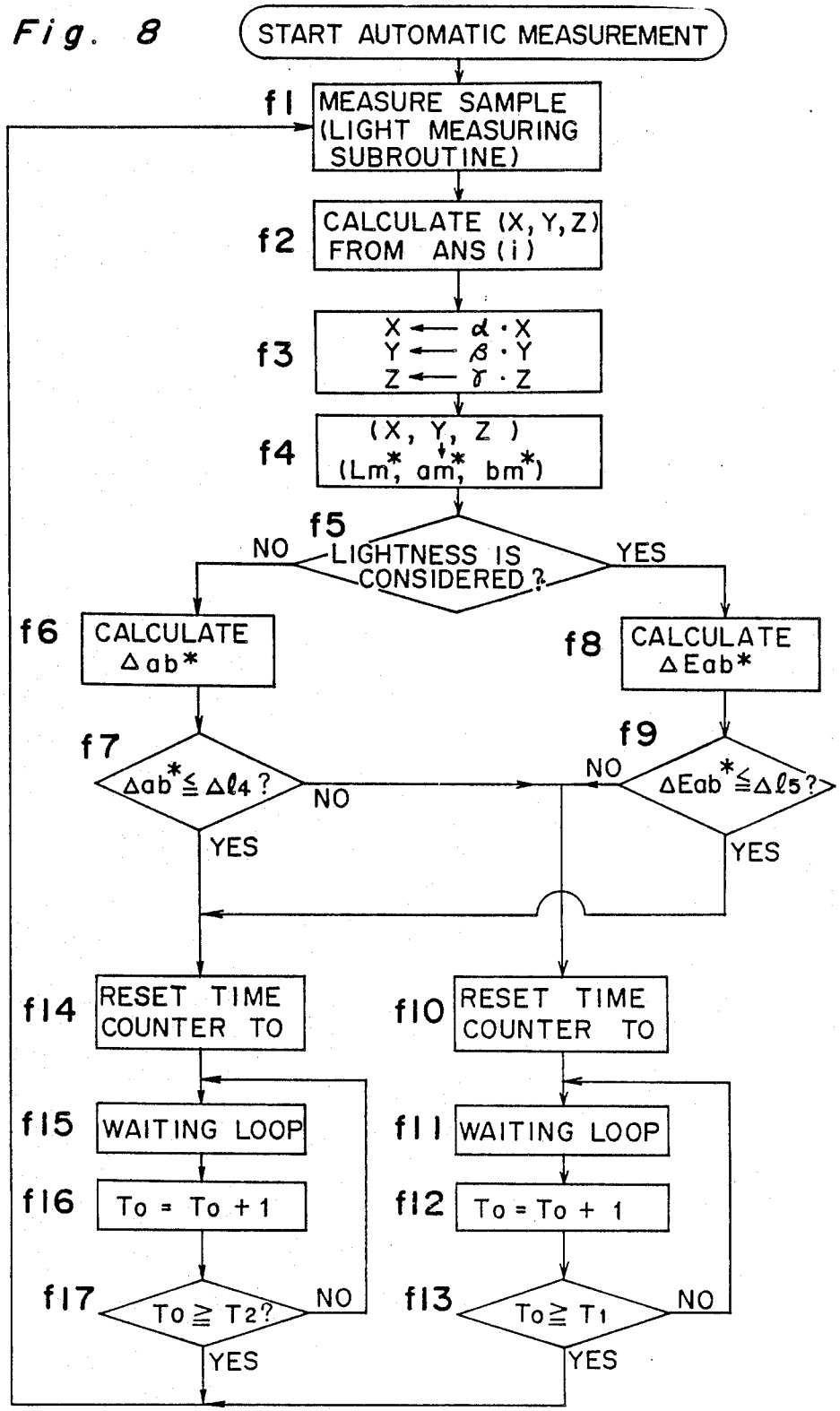
FIG. 8 is a flow chart showing an automatic measurement routine used in the color measuring apparatus of FIG. 7.

After the above described settings have been completed, a routine of FIG. 8 is executed so as to perform automatic measurement of the sample such that color of the sample is monitored. In the routine of FIG. 8, the light measuring subroutine of FIG. 3 is executed at step f1 so as to measure the sample. Then, at step f2, the tristimulus values (X, Y, Z) are calculated from the results ANS(i) obtained at step f1. Subsequently, at step f3, the tristimulus values (X, Y, Z) are, respectively, multiplied by the calibration factors ($\alpha$, $\beta$, $\gamma$) such that the results of the multiplication are newly set as the tristimulus values. Then, at step f4, the new tristimulus values (X, Y, Z) obtained at step f3 are converted into chromaticity coordinates defined by the $L^*a^*b^*$ colorimetric system such that the measured color value $(Lm^*, am^*, bm^*)$ is outputted externally. At the same time, a decision is made as to which one of the regions the chromaticity point belongs to such that waiting for the next measurement is performed for a time period preset for that region. By repeating this operation, monitoring of the sample is performed. Meanwhile, at this time, it can also be so arranged that the result of the decision as to which one of the regions the chromaticity point belongs to is also outputted externally.

A decision as to whether or not the measured color value $(Lm^*, am^*, bm^*)$ of the sample falls within the set region is made based on two cases, i.e. one case in which the lightness $L^*$ is considered and the other case in which the lightness $L^*$ is not considered. If it is found at step f5 that the lightness $L^*$ is not considered, a color difference value $\Delta ab^*$ between the measured color value of the sample and the target color value is calculated in the chromaticity region $(a^*, b^*)$ at step f6 by using the following equation.

$$\Delta ab^* = \sqrt{(am^* - a_T^*)^2 + (bm^* - b_T^*)^2}$$

Then, at step f7, a decision is made as to whether or not the color difference value $\Delta ab^*$ is equal to or less than the preset distance $\Delta l4$. On the other hand, if it is found at step f5 that the lightness $L^*$ is considered, a color difference value $\Delta Eab^*$ between the measured color value of the sample and the target color value is calculated in the chromaticity coordinates region $(L^*, a^*, b^*)$ at step f8 by using the following equation.

$$\Delta Eab^* = \sqrt{(Lm^* - L_T^*)^2 + (am^* - a_T^*)^2 + (bm^* - b_T^*)^2}$$

Then, at step f9, a decision is made as to whether or not the color difference value $\Delta Eab^*$ is equal to or less than the present value $\Delta l5$.

In the case of "NO" at steps f7 and f9, it is decided that the measured color value of the sample falls out of the region. Then, at step f10, a time counter T 0 is reset. Subsequently, a waiting loop is executed for the number of times corresponding to the time interval T 1 at steps f11 to f13. Thereafter, the program flow returns to step f1. Meanwhile, in the case of "YES" at steps f7 and f9, it is considered that the measured color value of the sample falls within the region. Then, at step f14, the time counter T 0 is reset. Subsequently, a waiting loop is executed for the number of times corresponding to the time interval T 2 at steps f15 to f17. Thereafter, the program flow returns to step f1. Thus, the time interval for measurement can be changed according to whether or not the measured color value of the sample falls within the region.

Meanwhile, the second embodiment of the present invention can also be so modified that amount of change of the color value of the sample measured in the chromaticity coordinates on a predetermined XYZ colorimetric system is detected such that automatic measurement of the sample is performed by changing the time interval for measurement based on the amount of change.

As will be seen from the foregoing, the predetermined region is set in the chromaticity coordinates and the time interval for automatic measurement is changed according to whether or not the color value of the measured sample in the chromaticity coordinates falls within the set region. Thus, measurement in the set region can be performed finely or roughly. Therefore, in the case where the change of color of the sample is automatically monitored, it becomes possible to restrict the amount of the measured data to an actually necessary minimum level.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as being included therein.

What is claimed is:

1. A color measuring device comprising:
   a photoelectric conversion means which separates light from a sample into a plurality of predetermined basic color components so as to output basic color signals corresponding to quantities of light of the basic color components, respectively;
   a data processing means including:
   a calculating means for calculating, on the basis of the basic color signals from said photoelectric conversion means, chromaticity coordinates defined by a predetermined colorimetric system so as to calculate a color value of the sample,
   a target setting means for setting a target color value of the sample in the predetermined colorimetric system,
   a region setting means for setting a predetermined region containing the color value,
   a region decision means for deciding whether or not the color value calculated by said calculating means falls within the predetermined region set by said region setting means, and
   an approximation decision means for deciding, when it was decided by said region decision means that the color value calculated by said calculating means falls within the predetermined region, whether or not the color value calculated by said calculating means has reached its most approximated value to the target color value set by said target setting means; and
   an output means for outputting a result of the decision of said approximation decision means.

2. A color measuring apparatus as claimed in claim 1, wherein said approximation decision means includes a decision means which decides that the color value calculated by said calculating means has reached its most approximated value to the target color value set by said target setting means when a deviation between the color value calculated by said calculating means and the target color value set by said target setting means has changed from a decreasing state to an increasing state.

3. A color measuring apparatus comprising:
   a photoelectric conversion means for converting light from a sample into electrical signals; and
   a data processing means which performs data processing on the basis of the electric signals so as to obtain information on the light from the sample, the data processing means including:
   a storage means for storing a target set value for the information,
   a region setting means for setting a region containing the target set value,
   a region decision means for deciding whether or not the information obtained by said data processing means falls within the region, and an approximation decision means for deciding, when it was decided by said region decision means that the information obtained by said data processing means falls within the region, whether or not the information obtained by said data processing means has most approximated the target set value.

4. A color measuring apparatus as claimed in claim 3, wherein said photoelectric conversion means includes a photodetector means which separates the light from the sample into predetermined basic color components so as to output basic color signals corresponding to quantities of light of the basic color components, respectively, said data processing means including a calculating means for calculating, as the information, a color value on the basis of the basic color signals.

5. A color measuring apparatus as claimed in claim 3, wherein said approximation decision means includes a deviation decision means which decides, when it was decided by said region decision means that the information obtained by said data processing means falls within the region, that the information obtained by said data processing means has reached its most approximated value to the target set value if a deviation of the information of said data processing means from the target set value has changed from a decreasing state to an increasing state.

6. A color measuring apparatus as claimed in claim 5, wherein said deviation decision means includes a decision means which decides that the information obtained by said data processing means has reached its most approximated value to the target set value when the information is closely approximated to the target set value.

7. A color measuring apparatus comprising:
a photoelectric conversion means for converting light from a sample into electric signals; and
a data processing means which performs data processing on the basis of the electric signals so as to obtain information on the light from the sample, the data processing means including:
a region setting means for setting a predetermined region for the information on the light from the sample,
a region decision means for deciding whether or not the information obtained by said data processing means falls within the predetermined region, and
a control means for controlling a time interval of measurement of the sample, which actuates, when it is decided by said region decision means that the information obtained by said data processing means falls out of the region, said photoelectric conversion means, said data processing means, said region setting means and said region decision means at a first time interval so as to automatically repeat the measurement of the sample;
said control means actuating, when it is decided by said region decision means that the information obtained by said data processing means falls within the region, said photoelectric conversion means, said data processing means, said region setting means and said region decision means at a second time interval different from the first time interval so as to automatically repeat the measurement of the sample.

8. A color measuring apparatus as claimed in claim 7, wherein the second time interval is so set as to be shorter than the first time interval.

9. A color measuring apparatus comprising:
a photoelectric conversion means which separates light from a sample into a plurality of predetermined basic color components so as to output basic color signals corresponding to quantities of light of the basic color components, respectively; and
a data processing means including:
a calculating means which converts the basic color signals from said photoelectric conversion means into coordinates defined by a predetermined colorimetric system so as to calculate a color value of the sample,
a region setting means for setting a predetermined region in the colorimetric system,
a decision means for deciding whether or not the color value calculated by said calculating means falls within the predetermined region, and
a control means for controlling a time interval of measurement of the sample, which actuates, when it is decided by said decision means that the color value falls out of the predetermined region, said photoelectric conversion means, said calculating means, said region setting means and said decision means at a first time interval so as to automatically repeat measurement of the sample,
said control means actuating, when it is decided by said decision means that the color value falls within the predetermined region, said photoelectric conversion means, said calculating means, said region setting means and said decision means at a second time interval different from the first time interval so as to automatically repeat the measurement of the sample.

10. A color measuring apparatus comprising:
means for receiving light from an object;
color conversion means which separates the measurement light into a plurality of predetermined basic color components so as to output basic color signals, corresponding to quantities of light of the basic color components, respectively, representative of the object, and
a data processing means including:
a calculating means for calculating, on the basis of the basic color signals from said color conversion means, chromaticity coordinates defined by a predetermined colorimetric system set by the operator so as to calculate a color value for the object,
a target setting means for setting a predetermined target color value within the predetermined colorimetric system,
a region setting means for setting a predetermined region containing the target color value,
a region decision means for deciding whether or not the color value calculated by said calculating means from the object falls within the predetermined region set by said region setting means, and
an approximation decision means for deciding, when it is decided by said region decision means that the color value calculated by said calculating means falls within the predetermined region, whether or not the color value of the object calculated by said calculating means has reached the closest value it can reach to the target color value set by said target setting means and providing a representative signal of such decision.

11. A color measuring apparatus as claimed in claim 10 wherein said approximation decision means includes a decision means which decides that the color value calculated by said calculating means has reached its closest value to the target color value set by said target setting means when a deviation between the color value calculated by said target setting means has changed from a decreasing state to an increasing state.

12. A color measuring apparatus comprising:
  means for projecting light on an object;
  means for receiving light from the object;
  a conversion means which separates light from the object into a plurality of predetermined basic color components so as to output basic color signals corresponding to quantities of light of the basic color components, respectively;
  means for compensating for any variations in the projecting light effecting the basic color signals, and
  a data processing means including:
    a calculating means which converts the basic color signals into coordinates defined by a predetermined colorimetric system so as to calculate a color value of the object,
    a region setting means for setting a predetermined region in the colorimetric system,
    a decision means for deciding whether or not the color value calculated by said calculating means falls with the predetermined region, and
    a control means for controlling a time interval of measurement of the object when it is decided by said decision means that the color value falls into or out of the predetermined region to provide respective different time intervals of measurement for measurements within the predetermined region and outside of the predetermined region.

13. A color measuring method comprising the steps of:
  (a) receiving light from a sample and separating the light into a plurality of predetermined basic color components;
  (b) outputting basic color signals corresponding to quantities of light of the basic color components, respectively;
  (c) calculating, on the basis of the basic color signals, a color value of the sample for a predetermined colorimetric system;
  (d) setting a target color value of the sample in the predetermined colorimetric system;
  (e) setting a predetermined region containing the target color value;
  (f) judging whether or not the calculated color value of the sample falls within the predetermined region;
  (g) detecting, when it is judged that the calculated color value of the sample falls within the predetermined region, whether or not the calculated color value of the sample has reached its most approximated value to the target color value, and
  (h) outputting a result of the detection.

14. A color measuring method comprising the steps of:
  (a) converting light from a sample into an electrical signal;
  (b) obtaining information on the light from the sample on the basis of the electric signal;
  (c) storing a predetermined target value;
  (d) setting a region containing the target value;
  (e) judging whether or not the obtained information falls within the region, and
  (f) detecting, when it is judged that the information falls within the region, whether or not the information has reached its most approximated value to the target value.

15. A color measuring method comprising the steps of:
  (a) converting light from a sample into an electric signal;
  (b) obtaining information on the light from the sample on the basis of the electric signal;
  (c) setting a predetermined region for the information;
  (d) judging whether or not the information falls within the predetermined region;
  (e) setting a first time interval and a second time interval, which are different from each other, according to the judgment, and
  (f) repeating the above steps (a) to (e) during the next set time interval.

16. A color measuring method comprising the steps of:
  (a) separating light from a sample light into a plurality of predetermined basic color components;
  (b) outputting basic color signals corresponding to quantities of light of the basic color components, respectively;
  (c) calculating, on the basis of the basic color signals, a color value of the samples in a predetermined colorimetric system;
  (d) setting a predetermined region in the predetermined colorimetric system;
  (e) judging whether or not the color value falls within the predetermined region;
  (f) setting a first time interval and a second time interval, which are different from each other, according to the judgment, and
  (g) repeating the above steps (a) to (f) during the next set time interval.

17. A color measuring method comprising the steps of:
  (a) receiving light from an object;
  (b) separating the light received into a plurality of predetermined basic color components;
  (c) outputting basic color signals, corresponding to quantities of light of the basic color components, respectively, representative of the object;
  (d) calculating, on the basis of the basic color signals, a color value of the object in a predetermined colorimetric system set by the operator;
  (e) setting a predetermined target color value in the predetermined colorimetric system;
  (f) setting a predetermined region containing the target value;
  (g) judging whether or not the calculated color value falls within the predetermined region;
  (h) detecting, when it is judged that the calculated color value falls within the predetermined region, whether or not the color value of the object has reached the closest value it can reach to the target color value;

(i) providing, when it is judged that the calculated color value falls within the predetermined region, a signal representing such determination.

18. A color measuring method comprising the steps of:
   (a) projecting light on an object;
   (b) receiving light from the object;
   (c) separating the light received from the object into a plurality of predetermined basic color components;
   (d) outputting basic color signals corresponding to quantities of light of the basic color components, respectively;
   (e) compensating for any variation in the projecting light effecting the basic color signals;
   (f) calculating a color value of the object in a predetermined colorimetric system;
   (g) setting a predetermined region;
   (h) judging whether or not the calculated color value falls within the predetermined region, and
   (i) setting a time interval of measurement of the object when it is judged that the calculated color value falls into or out of the predetermined region to provide respective different time intervals of measurement for measurements within the predetermined regions and outside of the predetermined region.

19. A color measuring method for determining and outputting a color value of a sample comprising the steps of:
   (a) setting a target color value in a predetermined colorimetric system;
   (b) setting a target region in the predetermined colorimetric system;
   (c) setting a first time interval and a second time interval, which are different from each other;
   (d) separating light from a sample into a plurality of predetermined basic color components;
   (e) outputting basic color signals corresponding to quantities of light of the basic color components, respectively;
   (f) calculating, on the basis of the basic color signals, a color value of the sample in the predetermined colorimetric system;
   (g) determining whether or not the calculated color value falls within the target region;
   (h) waiting for a time period equal to the first time interval when the calculated color value falls within the target region or a time period equal to the second time interval when the calculated color value falls outside of the target region, and
   (i) repeating steps (d) to (h) at the end of the wait period.

20. A color measuring method for determining the outputting a color value of a sample comprising the steps of:
   (a) setting a target color value in a predetermined colorimetric system;
   (b) setting a target region in the predetermined colorimetric system;
   (c) separating light from a sample into a plurality of predetermined basic color components;
   (d) outputting basic color signals corresponding to quantities of light of the basic color components, respectively;
   (e) calculating, on the basis of the basic color signals, a color value of the sample in the predetermined colorimetric system;
   (f) detecting, in the predetermined colorimetric system, the amount of change in the calculated color value from a previously calculated color value;
   (g) setting, based on the detected amount of change in the calculated color value, a first time interval of measurement for use when the calculated color value falls within the target region and a second time interval of measurement for use when the calculated color value falls outside of the target region;
   (h) determining whether or not the calculated color value falls within the target region;
   (i) waiting for a time period equal to the first time interval when the calculated color value falls within the target region or a time period equal to the second time interval when the calculated color value falls outside of the target region, and
   (j) repeating steps (c) to (i) at the end of the wait period.

* * * * *